United States Patent [19]

Behney

[11] 4,269,190

[45] May 26, 1981

[54] METHOD OF AND CLAMP FOR APPLYING PRESSURE TO A SKIN REGION

[76] Inventor: Charles A. Behney, Box 4337, Bisbee, Ariz. 85603

[21] Appl. No.: 59,504

[22] Filed: Jul. 23, 1979

[51] Int. Cl.³ ............................................. A61B 17/08
[52] U.S. Cl. .................................... 128/325; 128/346
[58] Field of Search ............... 128/346, 322, 354, 321, 128/325, 335, 334 R; 251/10; 24/255 R, 261 R

[56] References Cited

U.S. PATENT DOCUMENTS

| | | | |
|---|---|---|---|
| 1,748,227 | 2/1930 | Hyams | 128/346 |
| 2,704,071 | 3/1955 | Becker | 128/346 X |
| 2,842,132 | 7/1958 | Soltero et al. | 128/346 X |
| 3,020,826 | 2/1962 | Silva | 24/261 R X |
| 3,326,217 | 6/1967 | Kerr | 128/325 |
| 3,783,635 | 1/1974 | Perez | 24/261 R X |
| 3,996,937 | 12/1976 | Williams | 128/346 X |
| 4,195,636 | 4/1980 | Behnke | 128/346 |

FOREIGN PATENT DOCUMENTS

| | | | |
|---|---|---|---|
| 119055 | 9/1918 | United Kingdom | 128/321 |
| 438414 | 1/1975 | U.S.S.R. | 128/346 |

Primary Examiner—Robert W. Michell
Assistant Examiner—Michael H. Thaler
Attorney, Agent, or Firm—Gerlach, O'Brien & Kleinke

[57] ABSTRACT

Pressure is applied to a loose skin region of the animal body by forming an elongated skin fold in the region and applying a clamp to the fold, such clamp including a pair of elongated clamping portions resiliently biased towards each other, and the clamping portions being disposed on opposite sides of the fold therealong and spaced inwardly from the outer margin of the fold so as to clamp the fold between the clamping portions and secure the clamp in place.

A skin clamp includes a pair of clamping arms and a manipulating handle, the arms each having an elongated clamping portion and a relatively short guiding portion at a leading end of the arm, such clamping portions lying adjacent to each other along their length for clamping a skin fold between them, such guiding portions diverging from each other for guiding a skin fold between the clamping portions, the handle including structure resiliently biasing the clamping portions toward each other, and the handle including parts movable towards each other by finger pressure to spread the clamping portions apart.

7 Claims, 8 Drawing Figures

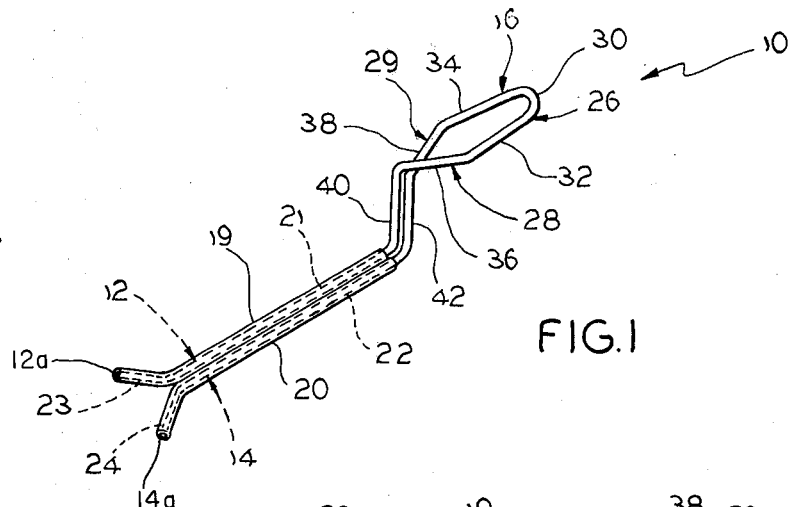
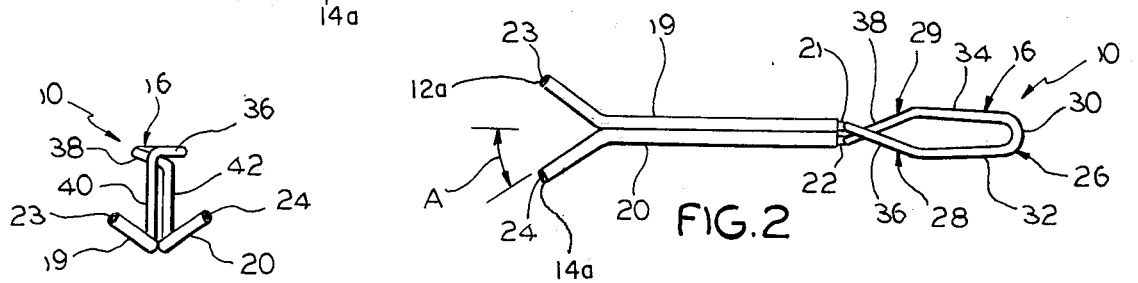
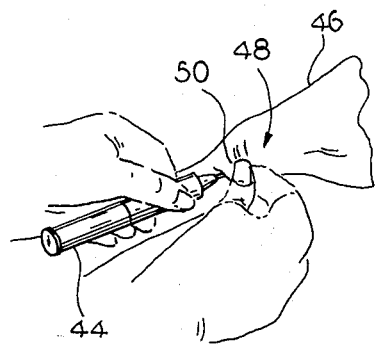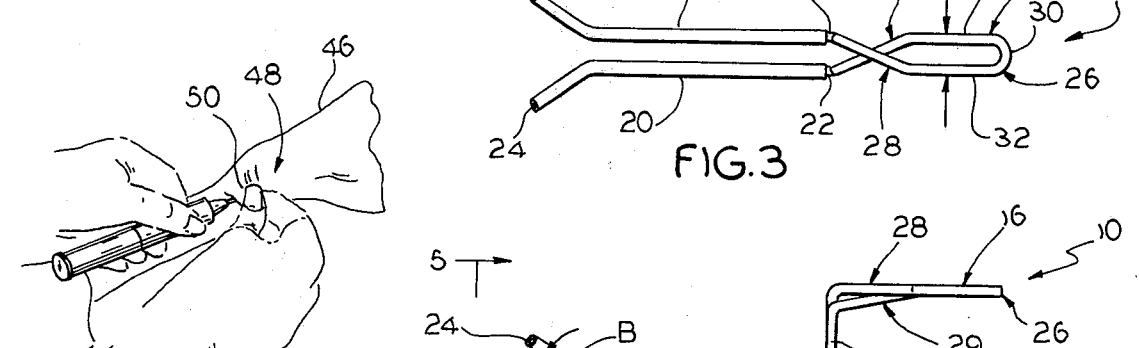
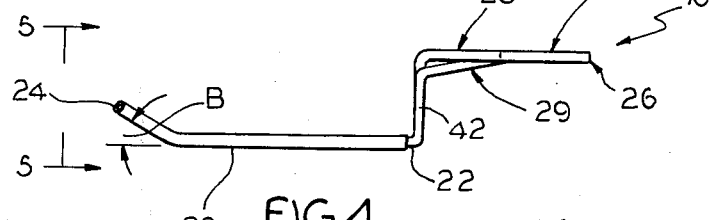
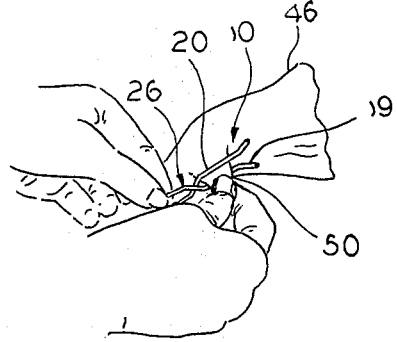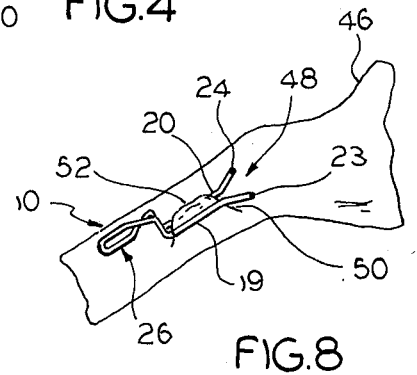

METHOD OF AND CLAMP FOR APPLYING PRESSURE TO A SKIN REGION

BACKGROUND OF THE INVENTION

This invention relates to a clamp for applying pressure to a skin region of the animal body. More particularly, the invention relates to a clamp especially useful for applying pressure to a skin region to prevent or control the flow of fluid through a puncture in a blood vessel or the skin, as may occur otherwise in connection with intravenous injection, blood drawing, or subcutaneous transfusion.

Venipuncture in loose skin regions, especially in small animals such as dogs and cats, frequently is accompanied by loss of blood which follows the needle out of the puncture in the vein and wells up beneath the skin to form a clot or hematoma, and also escapes through the puncture in the skin. When this happens, the vein cannot be located for a week or more, until the clot dissolves. Increasing difficulty in giving injections is experienced when daily treatments are required. The usual practice with small animals is to pinch the skin over a venipuncture with the fingers, commencing with the withdrawal of the needle and lasting for about two minutes. Bleeding still may occur, however, especially if the animal struggles.

Subcutaneous transfusions may be followed by a problem of leakage through the puncture in the skin, which is made with a larger needle, up to 14-16 gauge with the small animals. A large pressure pocket of fluid is present beneath the skin, which requires pinching the skin for a period of about 3-7 minutes for clot formation to close the hole. Leakage still may occur, however, especially if the animal struggles.

SUMMARY OF THE INVENTION

A skin clamp according to the invention, adapted for applying pressure to the skin to prevent or control fluid flow through a puncture, includes a pair of clamping arms extending from a manipulating handle, the arms each having an elongated clamping portion and a relatively short guiding portion at a leading end of the arm remote from the handle, the clamping portions lying adjacent to each other along their length for clamping a skin fold between them, the guiding portions diverging from each other towards the leading ends for guiding a skin fold between the clamping portions, the handle including means resiliently biasing the clamping portions towards each other, and the handle including parts movable towards each other by finger pressure to spread apart the clamping portions. Preferably, the guiding portions extend from the clamping portions laterally outwardly and towards the leading ends.

In a further preferred embodiment, the skin clamp is constructed of a length of spring wire bent to form a pair of clamping arms and a manipulating handle. Cushioning means preferably are provided on the clamping portion of each arm.

The skin clamp of the invention properly employed virtually eliminates the problems of hemorrhage following venipuncture and fluid leak following subcutaneous transfusion. The clamp is readily applied by the person making an injection or transfusion, following removal of the article or device used therefor.

The skin clamp is readily constructed to provide sufficient pressure on the skin and underlying blood vessels to prevent fluid flow through a puncture, without crushing the blood vessels. Such pressure also is adequate to prevent the skin from pulling through the clamp, particularly inasmuch as the fold produces an outer bend of greater thickness than the total thickness of the layers where they are pinched between the clamping arms.

The clamp is not uncomfortable, and as a result, an animal even though fully alert will not endeavor to remove it during the several minutes it must remain in place. Its small and unobtrusive nature also lends itself to use without annoyance to an animal.

The skin clamp is adapted especially for use on the skin of hairy animals, particularly dogs and cats. It is exceptionally simple and very economical, and it may be used in quantity and as a disposable item, if desired.

BRIEF DESCRIPTION OF THE DRAWINGS

The drawings illustrate preferred embodiments of the article of the invention, without limitation thereto. In the drawings, like elements are identified by like reference symbols in each of the views, and:

FIG. 1 is a top, front and side perspective view of a preferred embodiment of the skin clamp, shown approximately in full size as drawn;

FIG. 2 is a top plan view thereof;

FIG. 3 is a view like FIG. 2 but illustrating the clamp substantially as it appears when a manipulating handle thereof is squeezed to spread apart clamping portions of clamping arms in the skin clamp;

FIG. 4 is a side elevational view of the skin clamp embodiment;

FIG. 5 is a front end elevational view thereof, taken substantially on line 5—5 of FIG. 4; and FIGS. 6, 7 and 8 illustrate sequentially in the respective views several steps of a preferred embodiment of the method of the invention.

DESCRIPTION OF THE PREFERRED EMBODIMENTS

Referring to the drawings, particularly FIGS. 1-5, a skin clamp 10 constituting a preferred embodiment of the invention includes a pair of clamping arms 12 and 14, and a manipulating handle 16. Cushioning means in the form of tubular sleeves 19 and 20 are provided on the clamping arms 12 and 14.

The clamping arms 12 and 14 and the manipulating handle 16 in the illustrative preferred embodiment are formed of a length of spring wire, advantageously surgical stainless steel wire, such as Kirshner wire, bent to provide the arms and the handle in the illustrative configuration. An exemplary diameter for the wire is about 0.06 inch.

Each of the arms 12 and 14 includes a rearwardly disposed substantially straight or rectilinear elongated clamping portion 21 or 22 and a forwardly disposed relatively short straight guiding portion 23 or 24 at a leading end 12a or 14a of the arm remote from the handle 16. The clamping portions 21 and 22 lie adjacent to each other along their length or in side-by-side relation for clamping a skin fold between them. The guiding portions 23 and 24 diverge from each other towards the leading ends 12a and 14a, or forwardly, for guiding a skin fold between the clamping portions 21 and 22.

Referring to FIG. 2, each of the guiding portions 23 and 24 extends sidewise and forwardly from the integral clamping portion 21 or 22, at an acute angle A in the range of about 25-55 degrees, preferably about 40 degrees. The included angle between the guiding portions 23 and 24 thus is in the range of about 50-110 degrees, preferably about 80 degrees. Referring to FIG. 4, each of the guiding portions 23 and 24 extends laterally outwardly and forwardly from its integral clamping portion 21 or 22 at an acute angle B in the range of about 15-45 degrees, preferably about 30 degrees.

The clamping portions 21 and 22 in the illustrative clamp 10, especially well suited for use on dogs, preferably are in the range of about ¾ inch to 2 inches in length, and a preferred length is the illustrative length of about 1½ inches. The corresponding length of the guiding portions 24 preferably is about ⅜ inch and may be longer.

The manipulating handle 16 includes a bight or gripping portion 26 and connecting portions 28 and 29 integral with the bight portion at opposite ends thereof. The connecting portions 28 and 29 are integral with respective clamping portions 21 and 22 at trailing ends of the arms 12 and 14. The bight portion 26 includes a return bend 30 and slightly divergent (see FIG. 2) wing segments 32 and 34, which are urged apart by spring tension in the bend 30 and are movable towards each other. The connecting portions 28 and 29 include crossover segments 36 and 38 integral with the outer ends of the wind segments 32 and 34, respectively, one crossover segment 36 overlying the remaining such segment 38. The connecting portions 28 and 29 also include spacer segments 40 and 42 (see FIGS. 1 and 5) integral at opposite ends thereof with the crossover segments 36 and 38, and the clamping portions 21 and 22, respectively.

The spacer segments 40 and 42 extend substantially perpendicularly between the clamping portions 21 and 22, and the crossover segments 36 and 38, and are connected to such portions and segments by approximately right angle bends. In this manner, the bight or gripping portion 26 is spaced laterally outwardly from the clamping portions 21 and 22, and the bight portion 26 is substantially parallel to a plane in which the clamping portions 21 and 22 lie.

The cushioning sleeves 19 and 20 extend for the length of the clamping portions 21 and 22, and advantageously also for the length of the guiding portions 23 and 24. The sleeves cooperate with the spring tension in the clamp to prevent crushing of blood vessels while also making the clamp more comfortable. The sleeves are formed of relatively soft and resilient material, as compared to the remainder of the clamp, such as vinyl polymer, employed in the preferred embodiment, or other suitable plastic or elastomeric material, or the like.

The spring tension in the bent wire component of the clamp is predetermined to provide sufficient pressure exerted on a skin region between the clamping portions 21 and 22 to prevent or stop fluid flow through a puncture, such as the flow of blood or a transfusion fluid, without crushing the blood vessels, particularly the veins. The clamping portions 21 and 22 may be spread apart against the spring tension by applying pressure to the outer sides of the wing segments 32 and 34 of the bight portions 26, as illustrated in FIG. 3. This may be accomplished by squeezing the bight portion 26 between the thumb and a finger on one hand. The clamping portions 21 and 22 are approximately in parallel relation to each other as they come together, from the spread position of FIG. 3 to the contacting position of the sleeves 19 and 20 in FIG. 2. The parallel relation resulting from the configuration of the manipulating handle 16 constitutes a preferred condition, whereby approximately equal spring pressure is exerted along a skin fold clamped or pinched between the clamping portions 21 and 22.

FIGS. 6-8 illustrate a procedure employed in conjunction with the withdrawal of the needle of a hypodermic syringe 44 from a vein in a foreleg 46 of a dog. The vein is attached to the subcutaneous fascia in a loose skin region 48 of the leg. Following injection with the syringe 44, the skin and the vein thereunder are pinched between the thumb and forefinger of one hand, over the needle of the syringe and at the site of the puncture in the vein, and an elongated skin fold 50 is formed thereat by pulling the loose skin. The needle is withdrawn while continuing to apply finger pressure to the site of the puncture and maintain the skin fold, thereby to prevent escape of blood from the vein. A similar procedure is followed when a needle is withdrawn following a subcutaneous tranfusion, to prevent escape of fluid from beneath the skin.

Following withdrawal of the syringe needle, the clamp 10 is applied to the skin fold 50, in a manner such as illustrated in FIG. 7. The hand holding the fold continues to pinch the fold between the fingers, while the clamp 10 is applied by the other hand. The clamp 10 may be applied to smooth-haired dogs, such as beagles and terriers, merely by sliding it in place. Application to hairy dogs, such as poodles, sheep dogs, and huskies, may require that the clamping portions 21 and 22 be separated as described above, by squeezing the bight portion 26, so as to permit the clamp to move into place easily.

The divergency of the guiding portions 23 and 24 of the skin clamp 10, measured as the included angle 2A in FIG. 2, serves to guide the skin fold 50 between the clamping portions 21 and 22, and the sleeves 19 and 20 thereon. Such divergency also serves to collect the hair on the skin fold. The outward (as related to the leg 46) and forward (as related to the direction of movement of the clamp 10) inclination of the guiding portions 23 and 24 serves to avoid sticking the corresponding ends of the clamping arms 12 and 14 into the hair and skin, and perhaps pulling or gouging the same. The clamp 10 need merely be pushed against one end of the fold 50, with the guiding portions 23 and 24 on opposite sides thereof, whereupon the fold will enter the clamp between the clamping portions 21 and 22, until the clamp is in place, as illustrated in FIG. 8. The clamp is applied more readily to the hairy animals by squeezing the bight portion 26 at the same time, to separate the clamping portions 21 and 22, as illustrated in FIG. 3, whereby a fold 50 covered with more thickly matted hair may be accommodated without interference. The procedure is the same following a subcutaneous transfusion.

Referring to FIG. 8, when the clamp 10 is applied, the clamping portions 21 and 22 are disposed on opposite sides of the fold 50 therealong. The clamping portions 21 and 22 are spaced inwardly from the outer margin 52 of the fold 50, so as to extend over the portion of the vein embraced by the fold, clamp the fold and the vein portion between the clamping portions, and secure the clamp 10 in place. Forming a fold 50 of substantial extent along the leg 46 and pulled out therefrom insures that the vein is adequately clamped between the clamping portions 21 and 22. The reversely bent outer margin 52 of the skin fold 50 normally is somewhat thicker than the areas inwardly thereof, so that the skin is prevented from pulling out of the clamp 10. The clamp 10 is removed after a period of time sufficient for the puncture in the vein to be closed. Thereafter, the same vein may be located and punctured readily when additional treatment or examination is required. When the clamp 10 is applied following a subcutaneous transfusion, the clamp is removed after allowing sufficient time for the skin puncture to be closed.

While preferred embodiments of the article of the invention have been illustrated and described, it will be apparent to those skilled in the art that variations, changes and modifications may be made therein within the spirit and scope of the invention. It is intended that such variations, changes and modifications be included within the scope of the appended claims.

I claim:

1. A skin clamp which comprises: a manipulating handle including a gripping portion, a pair of clamping arms extending forwardly from said handle, each of said arms having a rearwardly disposed elongated clamping portion and a forwardly disposd relatively short guiding portion, said clamping portions lying adjacent to each other along their length in a plane for clamping a skin fold between them, and means resiliently biasing said clamping portions towards each other along their length, said guiding portions extending forwardly from said clamping portions and outwardly from the plane of the clamping portions to one side of such plane, said guiding portions diverging forwardly for guiding a skin fold between the clamping portions, said gripping portion being spaced outwardly from the clamping portions on said one side of the plane.

2. A skin clamp as defined in claim 1 and which comprises a length of spring wire bent to form said handle and said arms, and to provide said biasing means.

3. A skin clamp as defined in claim 1 or 2 and including cushioning means on each of said clamping portions.

4. A skin clamp which comprises: a length of spring wire bent to form a pair of clamping arms extending forwardly from a manipulating handle, each of said arms having a rearwardly disposed elongated clamping portion and a forwardly disposed relatively short guiding portion, said clamping portions lying adjacent to each other along their length in a plane for clamping a skin fold between them, said guiding portions extending forwardly from said clamping portions and outwardly from the plane of the clamping portions to one side of such plane, said guiding portions diverging forwardly for guiding a skin fold between the clamping portions, said handle including a bight portion connected to the rear ends of respective clamping portions, whereby the clamping portions are resiliently biased towards each other along their length.

5. A skin clamp as defined in claim 4 and wherein said handle includes connecting portions joined to opposite ends of said bight portion and to the rear ends of respective clamping portions, said connecting portions including segments extending outwardly from the plane of the clamping portions and to said one side of the plane to space said bight portion outwardly from the clamping portions.

6. A skin clamp as defined in claim 5 and wherein said connecting portions cross over each other, whereby the clamping portions may be spread apart by squeezing the bight portion.

7. A skin clamp as defined in claim 4, 5 or 6 and including a cushioning sleeve on each of said clamping portions.

* * * * *